United States Patent
Maeda et al.

(10) Patent No.: US 10,011,433 B2
(45) Date of Patent: Jul. 3, 2018

(54) WORKPIECE CONVEYOR SYSTEM

(71) Applicant: FANUC Corporation, Yamanashi (JP)

(72) Inventors: Yoshihide Maeda, Yamanashi (JP); Hiroshi Inutake, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 306 days.

(21) Appl. No.: 14/753,349

(22) Filed: Jun. 29, 2015

(65) Prior Publication Data

US 2015/0375351 A1 Dec. 31, 2015

(30) Foreign Application Priority Data

Jun. 30, 2014 (JP) .................................. 2014-135104

(51) Int. Cl.
*B23Q 7/14* (2006.01)
*B65G 37/00* (2006.01)
*B65G 25/04* (2006.01)
*G01N 35/04* (2006.01)

(52) U.S. Cl.
CPC ........... *B65G 37/005* (2013.01); *B65G 25/04* (2013.01); *G01N 35/04* (2013.01)

(58) Field of Classification Search
CPC ....... B65G 37/005; B65G 25/04; G01N 35/04
USPC .............................. 198/750.1, 750.14, 750.2
See application file for complete search history.

(56) References Cited

U.S. PATENT DOCUMENTS

| 4,625,854 | A | * | 12/1986 | Deichmann | B41F 17/18 198/416 |
|---|---|---|---|---|---|
| 6,126,380 | A | * | 10/2000 | Hillman | H01L 21/681 414/744.6 |
| 2003/0094349 | A1 | * | 5/2003 | Joutsjoki | B65G 25/04 198/750.1 |
| 2006/0120833 | A1 | * | 6/2006 | Bonora | H01L 21/67766 414/217 |

FOREIGN PATENT DOCUMENTS

| JP | 3-267220 A | 11/1991 |
|---|---|---|
| JP | H05-278835 A | 10/1993 |
| JP | 6-199417 A | 7/1994 |
| JP | 2009-226609 A | 10/2009 |

* cited by examiner

*Primary Examiner* — Michael S Lowe
(74) *Attorney, Agent, or Firm* — Hauptman Ham, LLP

(57) ABSTRACT

A workpiece convey system comprising two conveyor devices which alternately convey workpieces from a source area to a destination area, wherein each of the two conveyor devices is provided with a workpiece holding part which can hold a workpiece, and a movement mechanism which moves the workpiece holding part back and forth between the source area and the destination area, the two conveyor devices being arranged so as to match the positions where their respective workpiece holding parts are stopped within the source area.

6 Claims, 7 Drawing Sheets

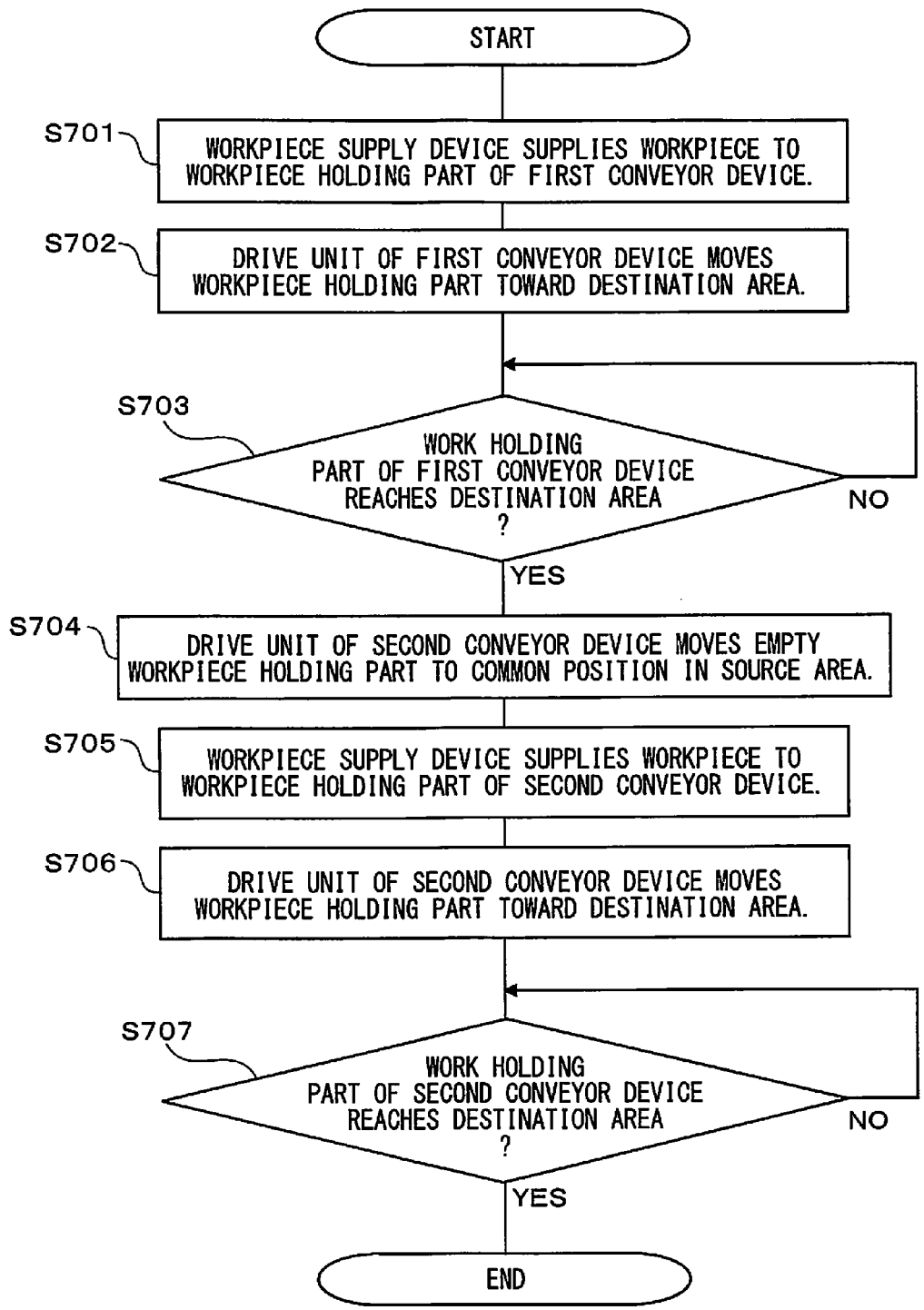

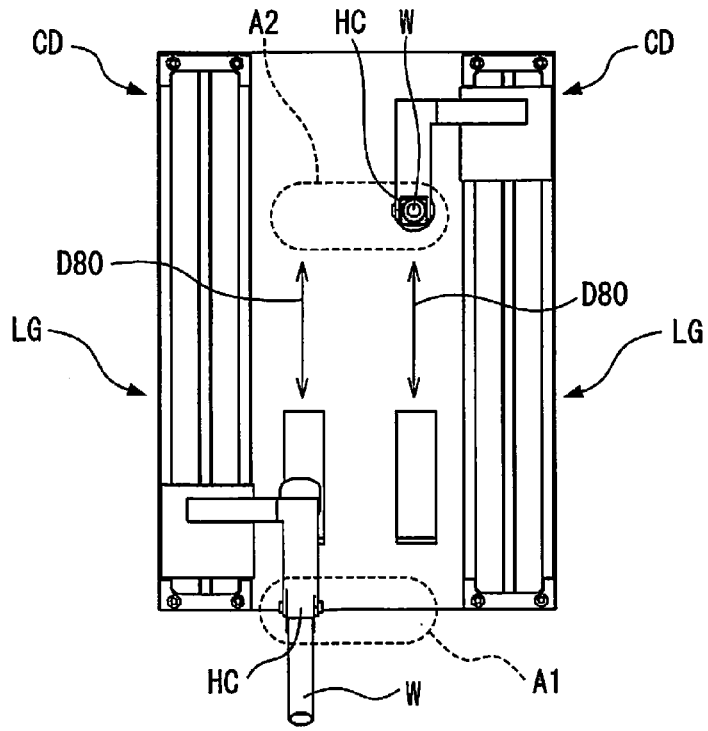
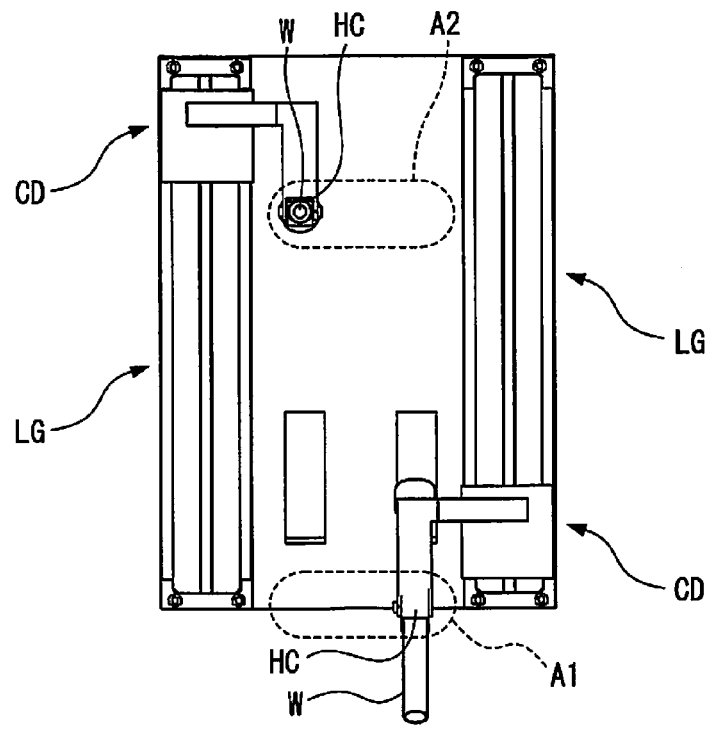

WORKPIECE CONVEYOR SYSTEM

RELATED APPLICATIONS

The present application claims priority to Japanese Application Number 2014-135104, filed Jun. 30, 2014, the disclosure of which is hereby incorporated by reference herein in its entirety.

BACKGROUND OF THE INVENTION

Field of the Invention

The present invention relates to a workpiece conveyor system comprising two conveyor devices which convey workpieces from a source area to a destination area.

An automation system which repeatedly conveys various workpieces from a source area to a destination area has been known in the prior art. For example, JP-A-H05-278835 proposes a workpiece conveyor system which conveys various workpieces which are stored on pallets by two conveyors which are arranged in series. In addition, a workpiece conveyor system is known which alternately conveys long workpieces like test tubes by two conveyor devices which are arranged in parallel. One example of such a conventional workpiece conveyor system is shown in FIG. 8 and FIG. 9.

FIG. 8 is a top view of the above-mentioned conventional workpiece conveyor system. As shown in FIG. 8, the conventional workpiece conveyor system is provided with two conveyor devices CD, CD which are arranged in a horizontal direction. These conveyor devices CD, CD are configured to convey workpieces W along mutually parallel paths. As shown in FIG. 8, each of the two conveyor devices CD, CD is provided with a tubular holding container HC which receives and holds part of a long workpiece W, and a linear guide LG which moves the holding container HC back and forth between a source area A1 and destination area A2. The directions of movement of the holding containers HC by the linear guides LG are shown by the arrows D80 in FIG. 8. FIG. 9 is a top view similar to FIG. 8 and shows the state where the holding container HC at the left side in FIG. 8 has been moved to the destination area A2 while the holding container HC at the right side has been moved to the source area A1.

As shown in FIG. 8 and FIG. 9, this conventional workpiece conveyor system uses two conveyor devices CD, CD to alternately convey workpieces W and can therefore shorten the cycle time which is required for the workpiece conveying process. However, in this conventional workpiece conveyor system, two holding containers HC, HC receive workpieces W at different positions from each other in the source area A1, and therefore a workpiece supply device which supplies workpieces to these holding containers HC, HC had to position the workpieces at two different positions. For this reason, in this conventional workpiece conveyor system, the problem arose that the supply process for supplying workpieces W to the holding containers HC is complicated. Furthermore, if additional processes were required for workpieces W which were supplied to the respective holding containers HC, the problem arose that these additional processes are also similarly complicated. The above "additional processes" include, for example, the process of filling a sample in a tubular workpiece W such as a test tube, the process of attaching a stopper to that workpiece W, the process of heating the workpiece W by a burner etc. to fuse the stopper, etc.

A workpiece conveyor system which can simplify the process of supplying workpieces to the two conveyor devices has been sought.

SUMMARY OF INVENTION

According to a first aspect of the present invention, there is provided a workpiece conveyor system comprising two conveyor devices which alternately convey workpieces from a source area to a destination area, wherein each of the two conveyor devices comprising a workpiece holding part which can hold a workpiece and a movement mechanism which moves the workpiece holding part back and forth between the source area and the destination area, the two conveyor devices being arranged so as to match the positions where their respective workpiece holding parts are stopped within the source area.

According to a second aspect of the present invention, there is provided a workpiece conveyor system of the first aspect, wherein the respective workpiece holding parts are changed in posture between the destination area and the source area.

According to a third aspect of the present invention, there is provided a workpiece conveyor system of the second aspect, further comprising an abutting member against which the respective workpiece holding parts are struck when being moved from the destination area to the source area, the respective workpiece holding parts are attached to the respective movement mechanisms so as to be able to rotate about predetermined rotation axes, and the respective workpiece holding parts are configured to be rotated about the rotation axis when being struck against the abutting member so that the respective workpiece holding parts are changed in posture.

According to a fourth aspect of the present invention, there is provided a workpiece conveyor system of the third aspect, wherein the rotation axes of the workpiece holding parts are parallel with each other.

These and other objects, features, and advantages of the present invention will become clearer with reference to the detailed description of an illustrative embodiment of the present invention which is shown in the attached drawings.

BRIEF DESCRIPTION OF THE DRAWINGS

FIG. 7 is a flow chart which shows a routine of an illustrative workpiece conveying process by a workpiece conveyor system of the present embodiment.

FIG. 8 is a top view of a conventional workpiece conveyor system.

FIG. 9 is a top view similar to FIG. 8 and shows a state where the holding container on the left side of FIG. 8 has been moved to the destination area and the holding container on the right side has been moved to the source area.

DETAILED DESCRIPTION OF EMBODIMENTS

Figure 1:
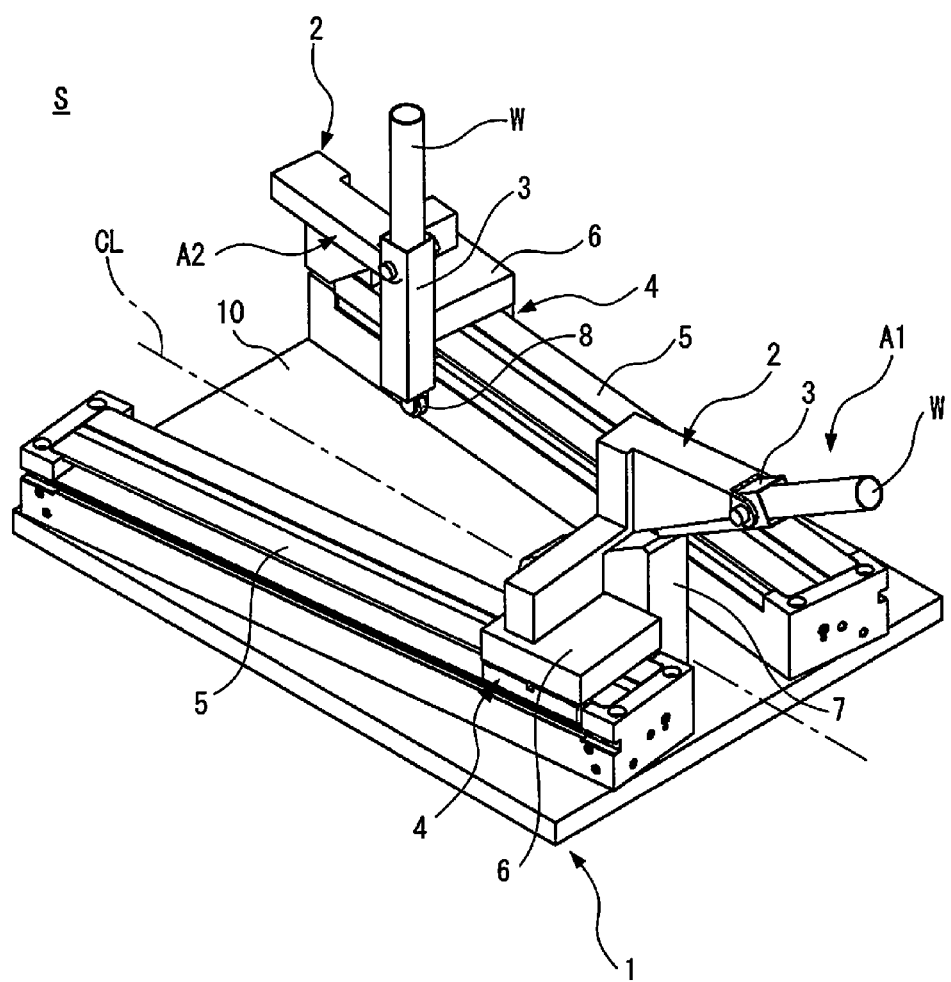
FIG. 1 is a first perspective view of an illustrative workpiece conveyor system according to an embodiment of the present invention.

Below, an embodiment of the present invention will be explained in detail with reference to the drawings. In the drawings, similar component elements are assigned similar reference notations. Note that the following explanation does not limit the technical scope of the inventions which are described in the claims or the meaning of terms etc.

Figure 2:
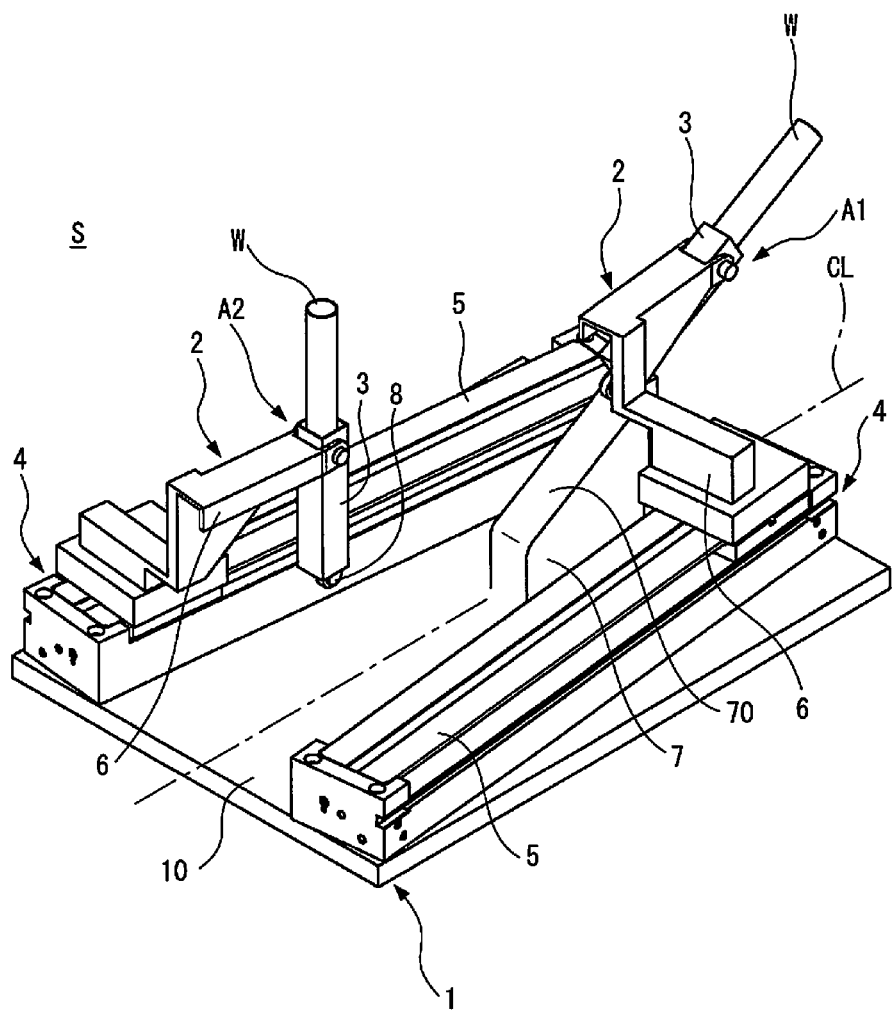
FIG. 2 is a second perspective view of the workpiece conveyor system of FIG. 1 seen from another direction.

Referring to FIG. 1 to FIG. 7, a workpiece conveyor system of one embodiment of the present invention will be explained. FIG. 1 is a first perspective view of an illustrative workpiece conveyor system S according to the present embodiment. The workpiece conveyor system S of this example is an automation system for conveying workpieces W which are supplied to a predetermined source area A1 to a predetermined destination area A2. The process of the workpiece conveyor system S of the present embodiment conveying the workpieces W will sometimes be referred to below as the "workpiece conveying process". FIG. 2 is a second perspective view of the workpiece conveyor system S of FIG. 1 seen from another direction.

As shown in FIG. 1 and FIG. 2, the workpiece conveyor system S of the present example is provided with a flat plate shaped main body 1, and two conveyor devices 2, 2 which are mounted on a single flat surface 10. These conveyor devices 2, 2 are configured to alternatively convey workpieces W which have been supplied to the source area A1 by an articulated robot or other workpiece supply device (not shown) to the destination area A2. The workpieces W which are conveyed by these conveyor devices 2, 2 are, for example, long tubular shaped members which have open ends. More specifically, they may be glass or plastic test tubes. The workpieces W which are conveyed by the conveyor devices 2, 2 to the destination area A2 are unloaded to the next process by an articulated robot or other workpiece unloading device (not shown). Below, the conveyor device 2 which is positioned on the left side of FIG. 1 will sometimes be referred to as the "first conveyor device 2", while the conveyor device 2 which is positioned on the right side of FIG. 1 will sometimes be referred to as the "second conveyor device 2".

Next, the specific structures of the two conveyor devices 2, 2 will be explained. As shown in FIG. 1 and FIG. 2, the two conveyor devices 2, 2 are arranged symmetrically on the both sides of a centerline CL of a flat surface 10 of the main body 1. Further, each of the two conveyor devices 2, 2 is provided with a workpiece holding part 3 which can hold a workpiece W and a movement mechanism 4 which moves the workpiece holding part 3 back and forth between the source area A1 and destination area A2. These elements will be explained below in order. First, the workpiece holding part 3 of the present example has a tubular form which is capable of receiving and holding part of the workpiece W in the extension direction. That is, the workpiece holding part 3 of the present example has a recessed part of a shape which corresponds to the workpiece W, and is configured to hold the workpiece W which has been inserted into that recessed part.

Further, each movement mechanism 4 of the present example comprises a plurality of mechanical components for moving the above workpiece holding part 3 back and forth along a predetermined path. More specifically, the movement mechanism 4 of the present example is a slide mechanism which is provided with a rail member 5 which is mounted on the flat surface 10 of the main body 1, and a slide member 6 which can move back and forth along the rail member 5. The above workpiece holding part 3 is attached to a predetermined location of the slide member 6. Further, the drive force of a motor or other drive unit (not shown) is used to move the slide member 6 back and forth between a start point and end point of the rail member 5, and thus move the workpiece holding part 3 which is attached to the slide member 6 back and forth between the source area A1 and the destination area A2. As shown in FIG. 1 and FIG. 2, two rail members 5, 5 are mounted on the flat surface 10 of the main body 1 so that the distance between the start points corresponding to the source area A1 is smaller than the distance between the end points corresponding to the destination area A2. That is, the two rail members 5, 5 are not parallel with each other but are inclined from each other by exactly a predetermined angle (see also FIG. 3 and FIG. 4).

While these workpiece holding parts 3 are moved back and forth in this way, the above workpiece supply device supplies workpieces W to the workpiece holding parts 3 which are stopped at the source area A1. The above workpiece unloading device unloads the workpieces W from the workpiece holding parts 3 which are stopped at the destination area A2. That is, these workpiece holding parts 3 are moved from the source area A1 to the destination area A2 while holding the workpieces W, then moved from the destination area A2 to the source area A1 without holding the workpieces W. Note that the two rail members 5, 5 in the present example both extend in straight line shapes on the flat surface 10, but one or both of the two rail members 5, 5 may also extend in curved line shapes on the flat surface 10.

Figure 3:
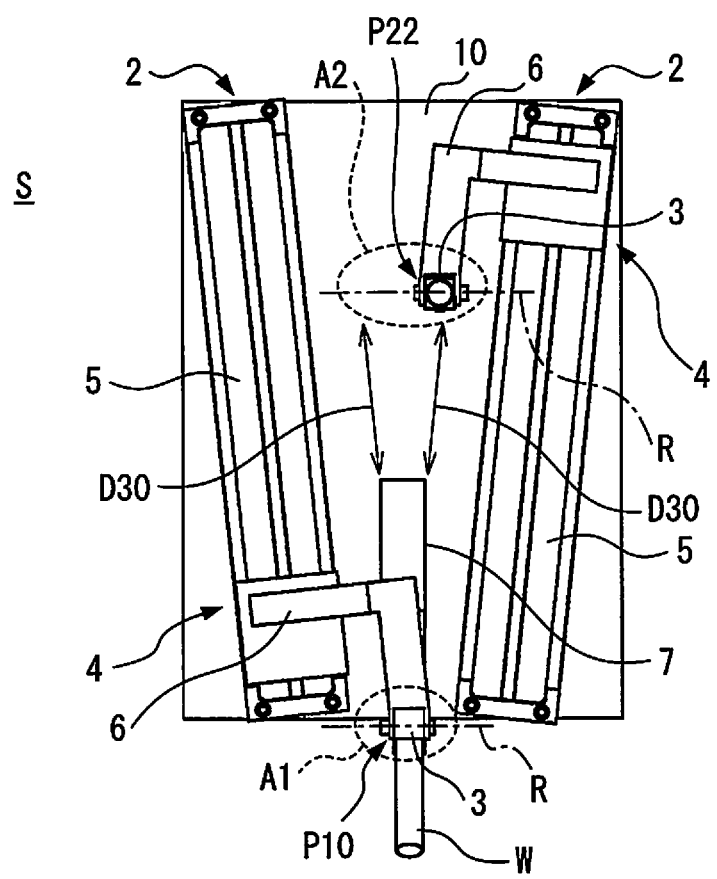
FIG. 3 is a first top view of the workpiece conveyor system of FIG. 1.
Figure 4:
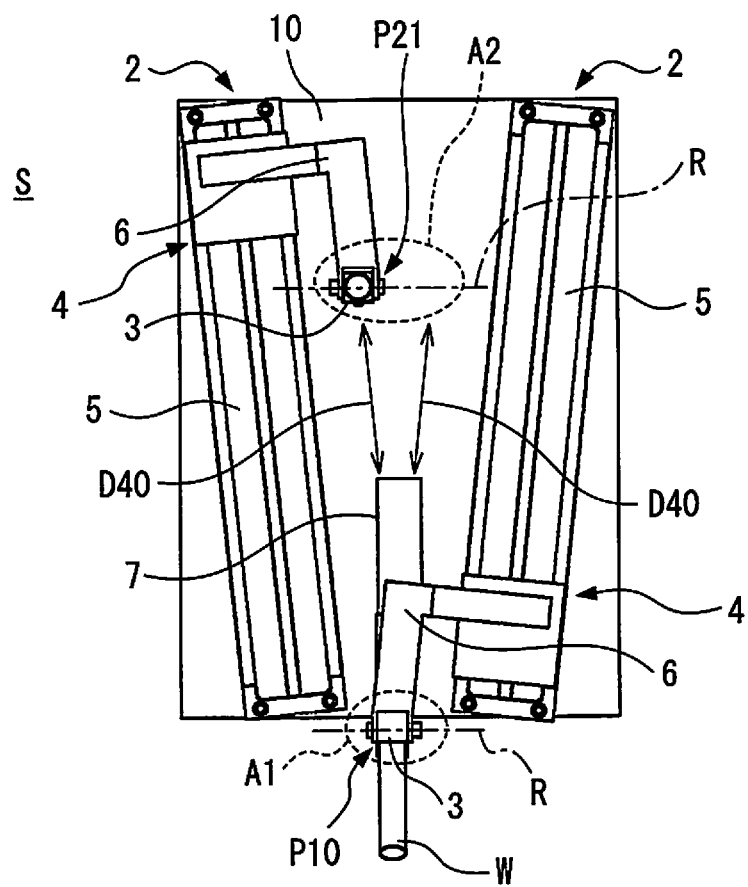
FIG. 4 is a top view similar to FIG. 3 and shows a state where a workpiece holding part of a first conveyor device is stopped at a destination area and a workpiece holding part of a second conveyor device is stopped at a source area.

Next, the specific layout of the two conveyor devices 2, 2 in the workpiece conveyor system S of the present embodiment will be explained. FIG. 3 is a top view of the workpiece conveyor system S of FIG. 1. FIG. 3, in the same way as FIG. 1 and FIG. 2, show the state where the workpiece holding part 3 of the first conveyor device 2 is stopped at the source area A1, and the workpiece holding part 3 of the second conveyor device 2 is stopped at the destination area A2. In FIG. 3, the directions of movement of these workpiece holding parts 3 are shown by the arrows D30. Further, FIG. 4 is a top view similar to FIG. 3 and shows the state where the workpiece holding part 3 of the first conveyor device 2 is stopped at the destination area A2, and the workpiece holding part 3 of the second conveyor device 2 is stopped at the source area A1. In FIG. 4, the directions of movement of these workpiece holding parts 3 are shown by the arrows D40. As shown in FIG. 3 and FIG. 4, the two conveyor devices 2, 2 are arranged on the flat surface 10 of the main body 1 so that the respective workpiece holding parts 3 are stopped at a common position P10 in the source area A1. The "common position P10" which is referred to here indicates the spatial position which the respective workpiece holding parts 3 as a whole occupy in the source area A1 when the respective workpiece holding parts 3 are stopped at the source area A1. In this way, this layout of the two conveyor devices 2, 2 ensures that the above workpiece supply device supplies the respective workpiece holding parts 3, 3 with workpieces W at a common position in the source area A1. Therefore, according to the above layout of the two conveyor devices 2, 2, it is possible to streamline the workpiece supply process where the workpiece supply device supplies workpieces W to the workpiece conveyor system S. Note that, as shown in FIG. 3 and FIG. 4, the two workpiece holding parts 3, 3 are stopped at the different positions P21, P22 from each other in the destination area A2.

Figure 5:
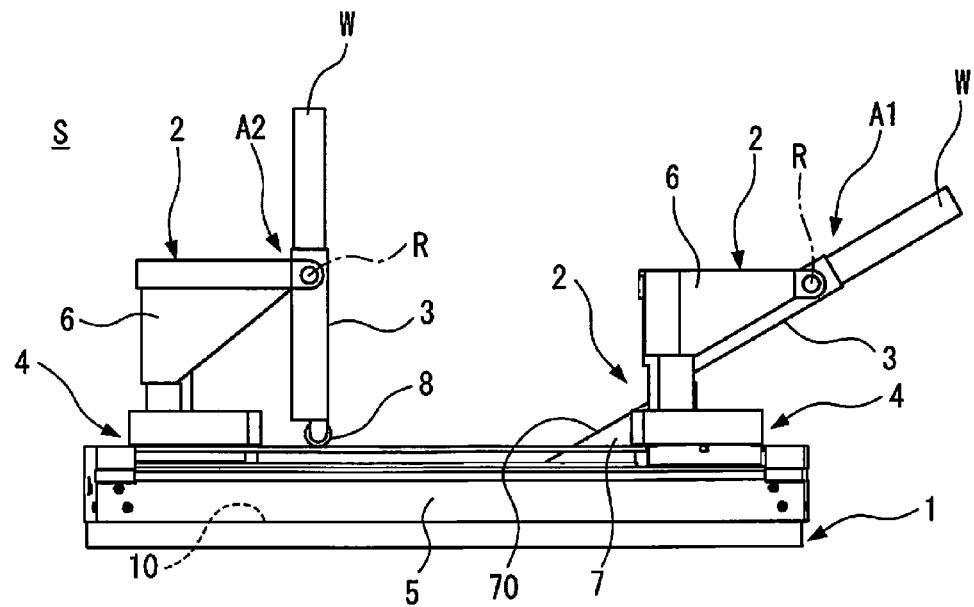
FIG. 5 is a side view of the workpiece conveyor system of FIG. 1.

Next, referring to FIG. 3 and FIG. 4, the workpiece conveyor system S of the present example is further provided with an abutting member 7, and the workpiece holding parts 3, 3 are configured to strike against the abutting member 7 while moving from the destination area A2 toward the source area A1 (see FIG. 1 and FIG. 2 as well). Here, FIG. 5 is a side view of the workpiece conveyor system S of FIG. 1. As shown in FIG. 2 and FIG. 5, the abutting member 7 of the present example is mounted near the source area A1 on the flat surface 10 of the main body 1, and has an inclined surface 70 which is inclined from the flat surface 10 of the main body 1 by a predetermined angle.

Further, as shown in FIG. 3 to FIG. 5, the respective workpiece holding parts 3 are attached to the slide members 6 of the respective movement mechanisms 4 so as to rotate about predetermined rotation axes R. Further, if these workpiece holding parts 3 strike the inclined surface 70 of the abutting member 7 while moving from the destination area A2 to the source area A1, the respective workpiece holding parts 3 will receive a reaction force from the inclined surface 70 of the abutting member 7 so as to be rotated about the rotation axes R. As shown in FIG. 1, FIG. 2, and FIG. 5, traveling members 8 such as balls or wheels which can travel on the inclined surface 70 of the abutting member 7 are attached to the bottom parts of the respective workpiece holding parts 3. This ensures that the respective workpiece holding parts 3 contact the inclined surface 70 through the running members 8 such as balls or wheels, and therefore the rotational motions of the workpiece holding parts 3 about the rotation axes R can be smoother.

As shown in FIG. 3 to FIG. 5, in the workpiece conveyor system S of the present example, the rotation axis R of one workpiece holding part 3 which is stopped at the workpiece source area A1 is parallel with the rotation axis R of the other workpiece holding part 3 which is stopped at the workpiece destination A2. Further, in the workpiece conveyor system S of the present example, the respective workpiece holding parts 3 are moved linearly along the flat surface 10, and therefore the rotation axes R, R of the two workpiece holding parts 3, 3 are maintained constantly parallel with each other without regardless of the positional relationship between the two workpiece holding parts 3, 3.

Figure 6:
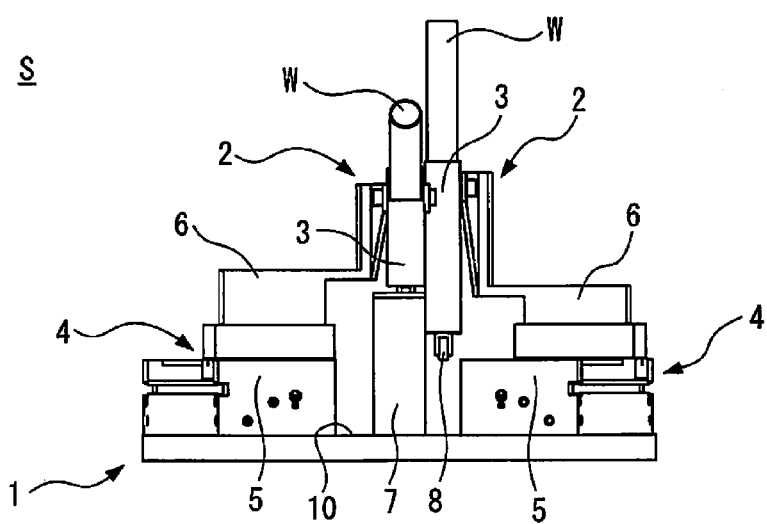
FIG. 6 is a front view of the workpiece conveyor system of FIG. 1.

The above structures of the workpiece holding parts 3 and abutting member 7 ensure that the respective workpiece holding parts 3 are changed in posture between the destination area A2 and the source area A1. Here, FIG. 6 is a front view of the workpiece conveyor system S of FIG. 1. As shown in FIG. 5 and FIG. 6, a workpiece holding part 3 which is stopped at the destination area A2 is oriented generally vertically with respect to the flat surface 10 of the main body 1, while a workpiece holding part 3 which is stopped at the source area A1 is oriented along the inclined surface 70 of the abutting member 7. Therefore, a workpiece holding part which is stopped at the source area A1 is inclined with respect to the flat surface 10 of the main body 1 by a predetermined angle. In this way, according to the workpiece conveyor system S of the present example, it is possible to change the postures of the respective workpiece holding parts 3 between the destination area A2 and the source area A1 in conjunction with the workpiece conveying process and without using a special drive source.

By suitably adjusting the postures of the respective workpiece holding parts 3 at the source area A1, it is possible to streamline the additional processes to be performed on the workpieces W which are supplied to the respective workpiece holding parts 3. The above additional processes include, for example, the process of filling a sample in a tubular workpiece W such as a test tube, the process of attaching a plug to that workpiece W, the process of heating the workpiece W by a burner etc. to fuse the plug, etc. The postures of the respective workpiece holding parts 3 at the source area A1 are adjusted in accordance with the shape, arrangement, etc. of the abutting member 7. For example, they can be adjusted in accordance with the inclination angle of the inclined surface 70 with respect to the flat surface 10. Furthermore, the rotation axes R, R of the two workpiece holding parts 3, 3 are parallel with each other, and therefore even if the postures of the respective workpiece holding parts 3 are changed between the destination area A2 and the source area A1, it is possible to easily match the positions where the respective workpiece holding parts 3 are stopped within the source area A1.

Next, the workpiece conveying process according to the workpiece conveyor system S of the present embodiment will be explained. FIG. 7 is a flow chart which shows the specific routine of an illustrative workpiece conveying process according to the workpiece conveyor system S of the present embodiment. As shown in FIG. 7, first, at step S701, a workpiece supply device such as an articulated robot supplies a workpiece W to the workpiece holding part 3 of the first conveyor device 2 which is stopped at the common position P10 in the source area A1 (see FIG. 3). At this point of time, the workpiece holding part 3 of the second conveyor device 2 is stopped at the position P22 within the destination area A2. Next, at step S702, the drive unit of the first conveyor device 2 moves the workpiece holding part 3 which holds the workpiece W toward the destination area A2. Further, when the workpiece holding part 3 of the first conveyor device 2 reaches the position P21 within the destination area A2 (step S703, YES), the drive unit of the second conveyor device 2 moves the empty workpiece holding part 3 which does not hold a workpiece W from the position P22 in the destination area A2 to the common position P10 within the source area A1 (step S704).

Next, at step S705, a workpiece supply device such as an articulated robot supplies a workpiece W to the workpiece holding part 3 of the second conveyor device 2 which is stopped at the common position P10 in the source area A1 (see FIG. 4). Next, at step S706, the drive unit of the second conveyor device 2 moves the workpiece holding part 3 which holds the workpiece W toward the destination area A2. Further, when the workpiece holding part 3 of the second conveyor device 2 reaches the position P22 within the destination area A2 (step S707, YES), the workpiece conveyor system S ends a cycle of the workpiece conveying process. In this cycle, the two workpieces W are conveyed from the source area A1 to the destination area A2. When the workpiece conveyor system S continues conveying workpieces W, the routine of the above steps S701 to S707 is repeatedly performed.

EFFECT OF INVENTION

According to the first aspect of the present invention, it is possible to match the workpiece supply positions where respective workpiece holding parts are supplied with workpieces by a workpiece supply device in the source area. Therefore, according to the first aspect, the workpiece supply device no longer has to supply workpieces at two different positions in the source area, and therefore it is possible to simplify the workpiece supply process for supplying workpieces to the two workpiece holding parts.

According to the second aspect of the present invention, it is possible to simplify additional processes to be performed on the workpieces which are supplied to the workpiece holding parts if the postures of the workpiece holding parts are suitably adjusted in the source area.

According to the third aspect of the present invention, the workpiece holding parts are changed in posture when they strike the abutting member to be rotated about the rotation axes. Therefore, according to the third aspect, it is possible to perform the process of changing the postures of the workpiece holding parts between the destination area and the source area in conjunction with the workpiece conveying process and without using dedicated drive unit.

According to the fourth aspect of the present invention, even when the workpiece holding parts are changed in posture between the destination area and the source area, it is possible to easily match the positions where the workpiece holding parts are stopped in the source area.

The present invention is not limited to the above-mentioned embodiment and can be modified in various ways within the scope described in the claims. For example, the workpiece holding parts in the workpiece conveyor system of the present invention may be of forms different from the above tubular members and may be various suction pickup members which pick up workpieces by suction or various robot hands etc. which grip workpieces by multiple fingers. Further, the movement mechanisms in the workpiece conveyor system of the present invention may be systems of movement mechanisms different from the above slide mechanisms and may be ball screws which are driven by motors or other drive devices or cylinders which are driven by fluid pressure etc. Further, the dimensions, shapes, materials, etc. of the parts which were described in the above embodiments are only examples. Various dimensions, shapes, materials, etc. can be employed for achieving the effects of the present invention.

The invention claimed is:

1. A workpiece conveyor system, comprising two conveyor devices which alternately convey workpieces from a source area to a destination area,
    each of said two conveyor devices comprising:
        a workpiece holding part which can hold a workpiece, and
        a movement mechanism which moves said workpiece holding part back and forth between the source area and the destination area,
    said two conveyor devices being arranged so as to match the positions where their respective workpiece holding parts are stopped within the source area,
    wherein the respective workpiece holding parts are changed in posture between the destination area and the source area,
    the workpiece conveyor system further comprising an abutting member against which the respective workpiece holding parts are struck when being moved from the destination area to the source area,
    wherein the respective workpiece holding parts are attached to the respective movement mechanisms so as to be able to rotate about predetermined rotation axes, and
    wherein the respective workpiece holding parts are configured to be rotated about said rotation axes when being struck against said abutting member so that the respective workpiece holding parts are changed in posture, wherein
    the movement mechanism of each of said two conveyor devices comprises a rail member, and
    the rail member of one of said two conveyor devices is inclined at an angle relative to the rail member of the other of said two conveyor devices.

2. The workpiece conveyor system according to claim 1, wherein the rotation axes of the respective workpiece holding parts are parallel with each other.

3. The workpiece conveyor system according to claim 1, wherein at least one of the rail members extends in a curved line shape.

4. The workpiece conveyor system according to claim 1, further comprising:
    a main body having a surface on which said two conveyor devices are mounted,
    wherein said two conveyor devices are arranged symmetrically on both sides of a centerline of the surface of the main body.

5. The workpiece conveyor system according to claim 4, wherein the abutting member has an inclined surface which is inclined with respect to the surface of the main body by a predetermined angle.

6. The workpiece conveyor system according to claim 1, wherein each of said two conveyor devices further comprises a travelling member attached to a bottom part of the workpiece holding part, said travelling member configured to travel on a surface of the abutting member to cause the workpiece holding part to rotate about the respective rotation axis.

\* \* \* \* \*